(12) United States Patent
Venturino et al.

(10) Patent No.: US 10,968,054 B2
(45) Date of Patent: Apr. 6, 2021

(54) AIR ASSISTED PARTICULATE DELIVERY SYSTEM

(71) Applicant: Kimberly-Clark Worldwide, Inc., Neenah, WI (US)

(72) Inventors: Michael B. Venturino, Appleton, WI (US); Benjamin J. Jensen, Sherwood, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/642,206

(22) PCT Filed: Aug. 31, 2017

(86) PCT No.: PCT/US2017/049565
§ 371 (c)(1),
(2) Date: Feb. 26, 2020

(87) PCT Pub. No.: WO2019/045720
PCT Pub. Date: Mar. 7, 2019

(65) Prior Publication Data
US 2020/0354165 A1 Nov. 12, 2020

(51) Int. Cl.
*B65G 53/10* (2006.01)
*B65G 53/52* (2006.01)
*A61F 13/15* (2006.01)

(52) U.S. Cl.
CPC ...... *B65G 53/521* (2013.01); *A61F 13/15658* (2013.01); *B65G 2201/042* (2013.01); *B65G 2812/165* (2013.01); *B65G 2812/1625* (2013.01)

(58) Field of Classification Search
CPC ........ B65G 51/03; B65G 53/10; B65G 53/28; B65G 53/42; B65G 49/065; B65G 2207/06

(Continued)

(56) References Cited

U.S. PATENT DOCUMENTS 1,515,965 A * 11/1924 Pardee .................... B07B 13/11
                                                                    209/697
2,316,814 A *  4/1943 Schemm ................ B65G 53/22
                                                                    406/89

(Continued)

FOREIGN PATENT DOCUMENTS

EP           0063960 A2   11/1982
SU           1221118 A1    3/1986
(Continued)

OTHER PUBLICATIONS

Dynamic Air, "Dyna-Slide Air-Activated Gravity Conveyor Series 126", www.dynamicair.com, 2016.

(Continued)

*Primary Examiner* — Joseph A Dillon, Jr.
(74) *Attorney, Agent, or Firm* — Kimberly-Clark Worldwide, Inc.

(57) ABSTRACT

Methods and apparatuses for conveying particulate material are described. A particulate material conveying apparatus may comprise a slide duct having a slide duct axis. The slide duct may comprise an interior region, and the interior region may have a top third interior region, a middle third interior region, and a bottom third interior region. The top third interior region is disposed above the middle third interior region and the middle third interior region is disposed above the bottom third interior region. The duct further defines an opening. An air movement mechanism may be connected to the duct an configured to move air through the opening into the slide duct in a direction of the slide duct axis such that a greater amount of air exits through the bottom third interior region than either of the top third interior region or the middle third interior region.

18 Claims, 8 Drawing Sheets

(58) Field of Classification Search
USPC .......... 406/87, 88, 144, 146, 151, 152, 153; 414/676; 108/50.13
See application file for complete search history.

(56) References Cited

U.S. PATENT DOCUMENTS

| | | | | |
|---|---|---|---|---|
| 2,330,642 A * | 9/1943 | Tuttle | ............. | B65D 88/32 414/272 |
| 3,338,992 A * | 8/1967 | Kinney | ............. | D01D 5/08 264/441 |
| 3,502,538 A * | 3/1970 | Petersen | ............. | D04H 3/12 428/359 |
| 3,502,763 A * | 3/1970 | Hartmann | ............. | D04H 3/015 264/555 |
| 3,542,615 A * | 11/1970 | Dobo | ............. | D04H 3/14 156/181 |
| 3,603,646 A * | 9/1971 | Leoff | ............. | B65G 51/03 406/89 |
| 3,692,618 A * | 9/1972 | Dorschner et al. | ... | B32B 37/144 442/401 |
| 3,802,817 A * | 4/1974 | Matsuki | ............. | D04H 3/03 425/66 |
| 3,849,241 A * | 11/1974 | Butin | ............. | D04H 3/007 428/137 |
| 3,948,564 A * | 4/1976 | Flint | ............. | B65G 51/03 406/31 |
| 4,100,324 A * | 7/1978 | Anderson | ............. | C11D 17/049 156/167 |
| 4,340,563 A * | 7/1982 | Appel | ............. | B32B 37/15 264/518 |
| 4,525,107 A * | 6/1985 | Feldsted | ............. | B63B 27/24 406/109 |
| 4,640,810 A * | 2/1987 | Laursen | ............. | D04H 1/732 264/121 |
| 4,648,779 A | 3/1987 | Weitzman | | |
| 4,795,668 A * | 1/1989 | Krueger | ............. | B01D 39/1623 428/174 |
| 4,818,464 A * | 4/1989 | Lau | ............. | D01D 4/025 156/167 |
| 4,819,928 A | 4/1989 | Osborn et al. | | |
| 4,934,875 A | 6/1990 | Fuss | | |
| 5,033,914 A * | 7/1991 | Wuertele | ............. | B65G 53/28 406/109 |
| 5,108,820 A * | 4/1992 | Kaneko | ............. | D04H 1/4291 428/198 |
| 5,284,703 A * | 2/1994 | Everhart | ............. | A61F 13/537 442/401 |
| 5,336,552 A * | 8/1994 | Strack | ............. | D04H 1/559 442/361 |
| 5,350,624 A * | 9/1994 | Georger | ............. | D04H 1/56 428/219 |
| 5,382,400 A * | 1/1995 | Pike | ............. | D04H 3/14 264/168 |
| 5,425,987 A * | 6/1995 | Shawver | ............. | D04H 1/559 442/334 |
| 5,429,788 A | 7/1995 | Ribble et al. | | |
| 5,540,992 A * | 7/1996 | Marcher | ............. | D01F 8/06 442/334 |
| 5,829,597 A | 11/1998 | Bielagus | | |
| 6,228,906 B1 | 5/2001 | Freakley | | |
| 6,402,436 B1 * | 6/2002 | Murphy | ............. | B65H 23/24 406/197 |
| 6,810,297 B2 | 10/2004 | Adin et al. | | |
| 7,185,748 B2 * | 3/2007 | Malatesta | ............. | B65H 29/60 193/8 |
| 7,597,185 B1 * | 10/2009 | Fortenbery | ............. | B65G 11/123 193/25 A |
| 7,803,244 B2 * | 9/2010 | Siqueira | ............. | B32B 38/04 156/229 |
| 8,376,663 B2 * | 2/2013 | Erceg | ............. | B65G 51/03 406/88 |
| 9,469,495 B2 | 10/2016 | Caspar | | |
| 9,480,282 B2 * | 11/2016 | Levy | ............. | A24B 3/16 |
| 2001/0031176 A1 * | 10/2001 | Rassman, Jr. | ............. | B65G 51/02 406/153 |
| 2002/0187012 A1 * | 12/2002 | Grasshoff | ............. | B65G 53/28 406/95 |
| 2005/0005816 A1 | 1/2005 | Yamashita et al. | | |
| 2005/0058516 A1 | 3/2005 | Gille et al. | | |
| 2005/0098016 A1 | 5/2005 | Benuzzi | | |
| 2005/0265793 A1 * | 12/2005 | Van Mullekom | .... | B65G 53/521 406/10 |
| 2009/0269149 A1 * | 10/2009 | Hilgraf | ............. | B65G 53/28 406/155 |
| 2012/0213599 A1 | 8/2012 | Inazawa et al. | | |
| 2015/0197034 A1 | 7/2015 | Hauber et al. | | |

FOREIGN PATENT DOCUMENTS

| | | |
|---|---|---|
| SU | 1291511 A1 | 2/1987 |
| SU | 1346540 A1 | 10/1987 |
| SU | 1771459 A3 | 10/1992 |

OTHER PUBLICATIONS

Pack Air, Inc, "Air Conveyor", http://www.packairinc.come/products/air-conveyor/, Dec. 24, 2016.

* cited by examiner

AIR ASSISTED PARTICULATE DELIVERY SYSTEM

TECHNICAL FIELD

The present disclosure is directed toward particulate delivery systems, and more particularly to gravity-fed particulate delivery systems.

BACKGROUND OF THE DISCLOSURE

Absorbent articles, such as disposable infant diapers, feminine care products, incontinence garments and the like, include super absorbent particulate materials ("SAM") such as superabsorbent polymers which allow for increased absorbent capacity of the article and a reduction in the bulkiness of the article as compared to traditional absorbent material such as wood fluff. Various devices and processes have been employed to manufacture absorbent article designs including SAM. In some examples, a suction drum apparatus is used for making an absorbent core or pad wherein absorbent material, such as pulp fluff and SAM, is mixed together in a forming chamber and deposited onto the suction drum by gravity and/or suction of air through the suction drum.

In some examples, the SAM is fed into the forming chamber to be mixed with the pulp fluff through pneumatic conveyance means. For instance, the SAM is fed through a tube by high-speed air movement and pushed into the forming chamber by the movement of the air. In other examples, the SAM may be fed into the forming chamber by gravity conveyance. In such examples, a SAM hopper may be positioned above the forming chamber to allow the SAM to be fed along one or more SAM chutes leading into the forming chamber. Both SAM feeding processes, pneumatic conveyance and gravity conveyance, can result in un-even mixture of the SAM with the pulp fluff in the forming chamber and/or un-even deposition of the SAM onto the suction drum. This result can make it difficult to control the ultimate distribution of the SAM within the formed absorbent cores. Accordingly, methods and apparatuses are desired which can help to increase control of the SAM distribution within formed absorbent cores.

SUMMARY OF THE DISCLOSURE

The disclosure is directed to several alternative designs, materials and methods of manufacturing medical device structures and assemblies, and uses thereof.

In a first example, a particulate material conveying apparatus may comprise a slide duct extending between a proximal end and a distal end and having a slide duct axis extending in both a vertical direction and a horizontal direction. The slide duct may further comprise an interior region bounded at least in part by a slide duct wall, the interior region having a top third interior region extending along the slide duct axis, a middle third interior region extending along the slide duct axis, and a bottom third interior region extending along the slide duct axis, each interior region extending between the proximal end and the distal end of the slide duct, wherein the top third interior region is disposed above the middle third interior region in the vertical direction and wherein the middle third interior region is disposed above the bottom third interior region in the vertical direction, and an opening defined by the slide duct wall. The apparatus may further comprise an air movement mechanism configured to move air through the opening and into the interior region of the slide duct in a direction of the slide duct axis such that of the air exiting the slide duct distal end a greater amount of air exits through the bottom third interior region than either of the top third interior region or the middle third interior region.

In a second example, the particulate material conveying apparatus of claim 1 may have a majority of the air exiting the slide duct distal end may exit through the bottom third interior region.

In a third example, the proximal end of the slide duct of any of the first or second examples may define the opening.

In a fourth example, the opening of any of the first and second examples may comprise an aperture in the slide duct wall.

In a fifth example, the air movement mechanism of any of the first through fourth examples may comprise an air-knife.

In a sixth example, the particulate material conveying apparatus of any of the first through fifth examples may further comprise a particulate material outlet through which particulate material enters the interior region of the slide duct, and the particulate material outlet may be disposed closer to the distal end of the slide duct than the opening.

In a seventh example, the air movement mechanism of any of the first through sixth examples may be configured to supply air to the opening at a pressure of between about 1 pounds per square inch (psi) and about 25 psi.

In an eighth example, the air movement mechanism of any of the first through seventh examples may be configured to supply air to the opening at a pressure of between about 1 pounds per square inch (psi) and about 15 psi.

In a ninth example, the air movement mechanism of any of the first through eighth examples may be configured to supply air to the opening at a pressure of between about 1 pounds per square inch (psi) and about 5 psi.

In a tenth example, a particulate material conveying apparatus may comprise a slide duct extending between a proximal end and a distal end and having a slide duct axis extending in both a vertical direction and a horizontal direction, the slide duct comprising an interior region bounded at least in part by a slide duct wall, the slide duct wall defining an opening, and an air movement mechanism configured to move air through the opening and into the interior region of the slide duct, wherein the air enters the interior region of the slide duct at an angle of between about 0 degrees and about 30 degrees with respect to the slide duct axis. In some embodiments, the air movement mechanism may be configured to supply air to the opening at a pressure of between about 1 pounds per square inch (psi) and about 20 psi.

In an eleventh example, the air movement mechanism of the tenth example may comprise a nozzle, and the nozzle may be disposed proximate the opening and orientated at an angle of between about 0 degrees and about 10 degrees with respect to the slide duct axis.

In a twelfth example, the air movement mechanism of any of the tenth or eleventh examples may comprise an air-knife.

In a thirteenth example, the air movement mechanism of any of the tenth or eleventh examples may comprise an air blower.

In a fourteenth example, at least a portion of the interior region of the slide duct of any of the tenth through thirteenth examples may be under negative pressure.

In a fifteenth example, the material conveying apparatus of any of the tenth through fourteenth examples may further comprise a material outlet through which material enters the interior region of the slide duct, and the material outlet may be disposed closer to the distal end of the slide duct than the opening.

In a sixteenth example, the air movement mechanism of any of the tenth through fifteenth examples is may be configured to supply air to the opening at a pressure of between about 1 psi to about 25 psi.

In a seventeenth example, the air movement mechanism of any of the tenth through sixteenth examples may be configured to supply air to the opening at a pressure of between about 1 psi to about 15 psi.

In an eighteenth example, a particulate material conveying system may comprise a hopper connected to conduit, the conduit extending between a proximal end connected to the hopper and a distal end, a slide duct extending between a proximal end and a distal end and having a slide duct axis, the slide duct comprising an interior region bounded at least in part by a slide duct wall, the slide duct wall defining an opening, an air movement mechanism configured to move air through the opening and into the interior region of the slide duct, and a vacuum source connected to the slide duct distal end. Additionally, the air movement mechanism may be configured to move the air into the interior region of the slide duct at an angle of between about 0 degrees and about 30 degrees with respect to the slide duct axis and configured to supply the air to the opening at a pressure of between about 1 pounds per square inch (psi) and about 25 psi. The conduit distal end is disposed between the slide duct proximal end and the slide duct distal end.

In a nineteenth example, the conduit distal end of the eighteenth example may be disposed closer to the slide duct distal end than the opening.

In a twentieth example, the air movement mechanism of any of the eighteenth and nineteenth examples may comprise an air knife.

The above summary of some example embodiments is not intended to describe each disclosed embodiment or every implementation of the aspects of the disclosure

BRIEF DESCRIPTION OF DRAWINGS

The aspects of the disclosure may be further understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION OF THE DISCLOSURE

The present disclosure is directed towards methods and apparatuses for delivering particulate material, such as SAM particles, into a forming chamber for forming an absorbent core of an absorbent article. The method can comprise delivering particulate material to the forming chamber along a slide duct, wherein the SAM particles descend the slide duct at least in part under the force of gravity. The slide duct may generally comprise an interior region bounded by slide duct walls and may have a proximal end where the duct may receive the particulate material and a distal end where the particulate material exits the duct. The duct interior region may be split into a top third interior region, a middle third interior region, and a bottom third interior region. The method may further comprise delivering air through the slide duct in the direction of particulate travel, wherein a majority of the delivered air exits the slide distal end through the bottom third interior region. In some embodiments, the delivered air may be delivered at a pressure of between about 1 pound per square inch (psi) and about 20 psi. Such a method of air delivery in a particulate material transport apparatus can help to increase a uniformity of distribution of the SAM particles as they exit the slide duct, and therefore allows for a more consistent control of the distribution of the SAM particles within the forming chamber and ultimately within formed absorbent cores.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Although some suitable dimensions, ranges and/or values pertaining to various components, features and/or specifications are disclosed, one of skill in the art, incited by the present disclosure, would understand desired dimensions, ranges and/or values may deviate from those expressly disclosed. Additionally, all numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. Further, the recitation of numerical ranges by endpoints includes all numbers within that range (e.g., 1 to 5 includes 1, 1.5, 2, 2.75, 3, 3.80, 4, and 5). As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

Definitions

As used herein, the term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, and incontinence products, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

The term "stretch film laminate" refers herein to a laminate of an elastic film laminated to at least one outer layer of fibrous nonwoven web material. Desirably, the elastic film is air and vapor permeable and liquid impermeable and elastic in at least one and preferably two directions generally perpendicular to one another. More desirably, the elastic film is elastic in all directions of the X-Y plane of the material. In other embodiments, the elastic film can have cover layers, such as fibrous nonwoven web materials laminated to both sides of the elastic film so as so form a laminate with opposed exterior nonwoven layers, an intermediate layer of elastic film bonded to both of the exterior nonwoven layers. Further information can be found with reference to U.S. Pat. No. 7,803,244 to Siqueira et al. and U.S. Pat. No. 8,361,913 to Siqueira et al., each of which is incorporated herein in its entirety by reference.

As used herein, the terms "superabsorbent polymer," "superabsorbent," or "SAM" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAM's ability to absorb water is based in part on ionicity (a factor of the ionic concentration of the aqueous solution), and the SAM functional polar groups that have an affinity for water. SAM are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAM may be present in absorbent articles in particle or fibrous form or as a coating or another material or fiber. Such SAM particles may be capable of absorbing at least about 15 times their weight and in some embodiment at least about 30 times their weight in an aqueous solution containing 0.9 weight percent sodium chloride.

The term "elasticated" when used herein to describe a material or a portion of an article means that the material or article it is made of an inelastic sheet material coupled to elastic material, e.g. one or more elastic bands or strands, such that the material or article exhibits elastic properties.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 1:
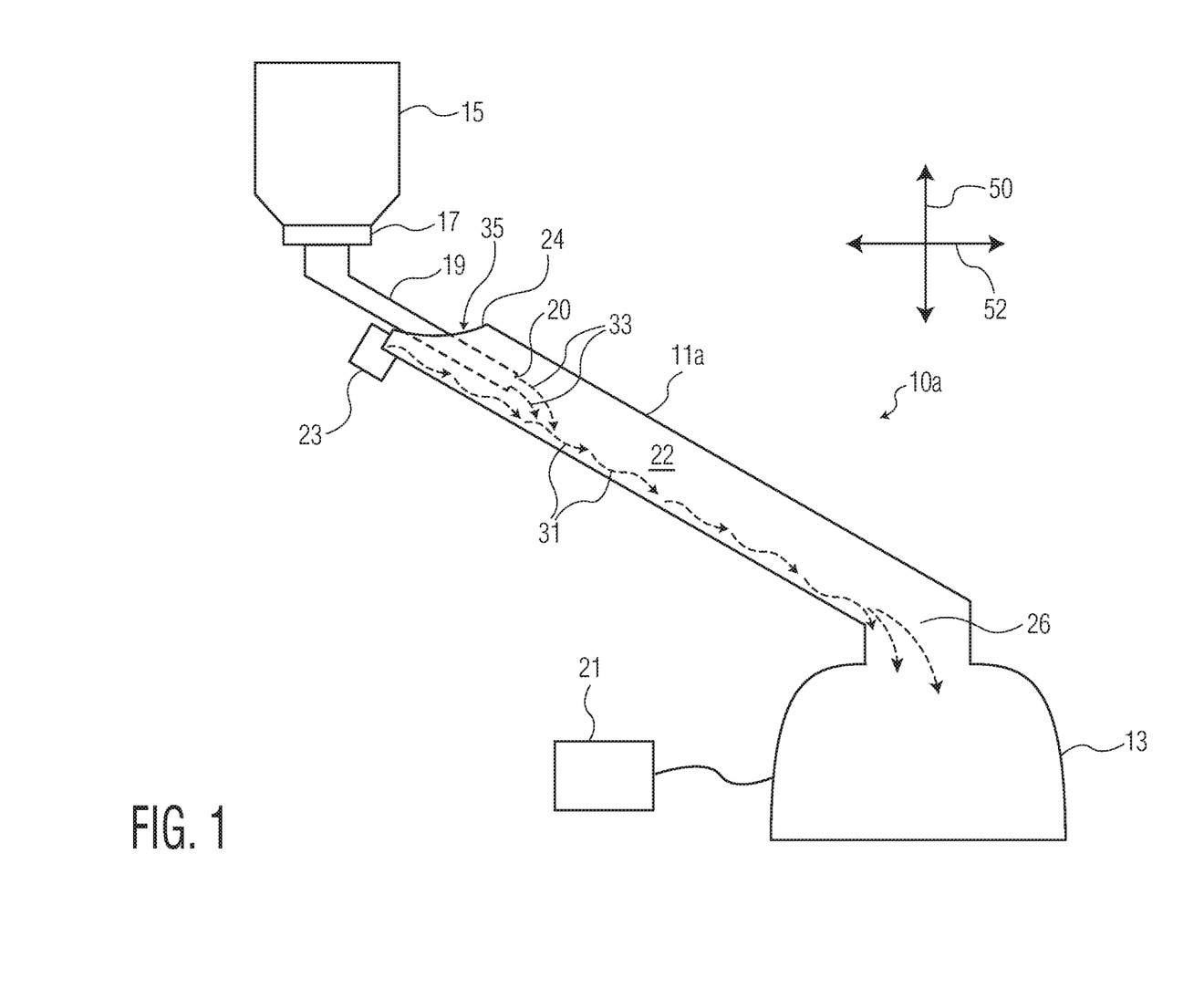
FIG. 1 is a diagram of an exemplary particulate material conveying system according to the present disclosure.
Figure 3:
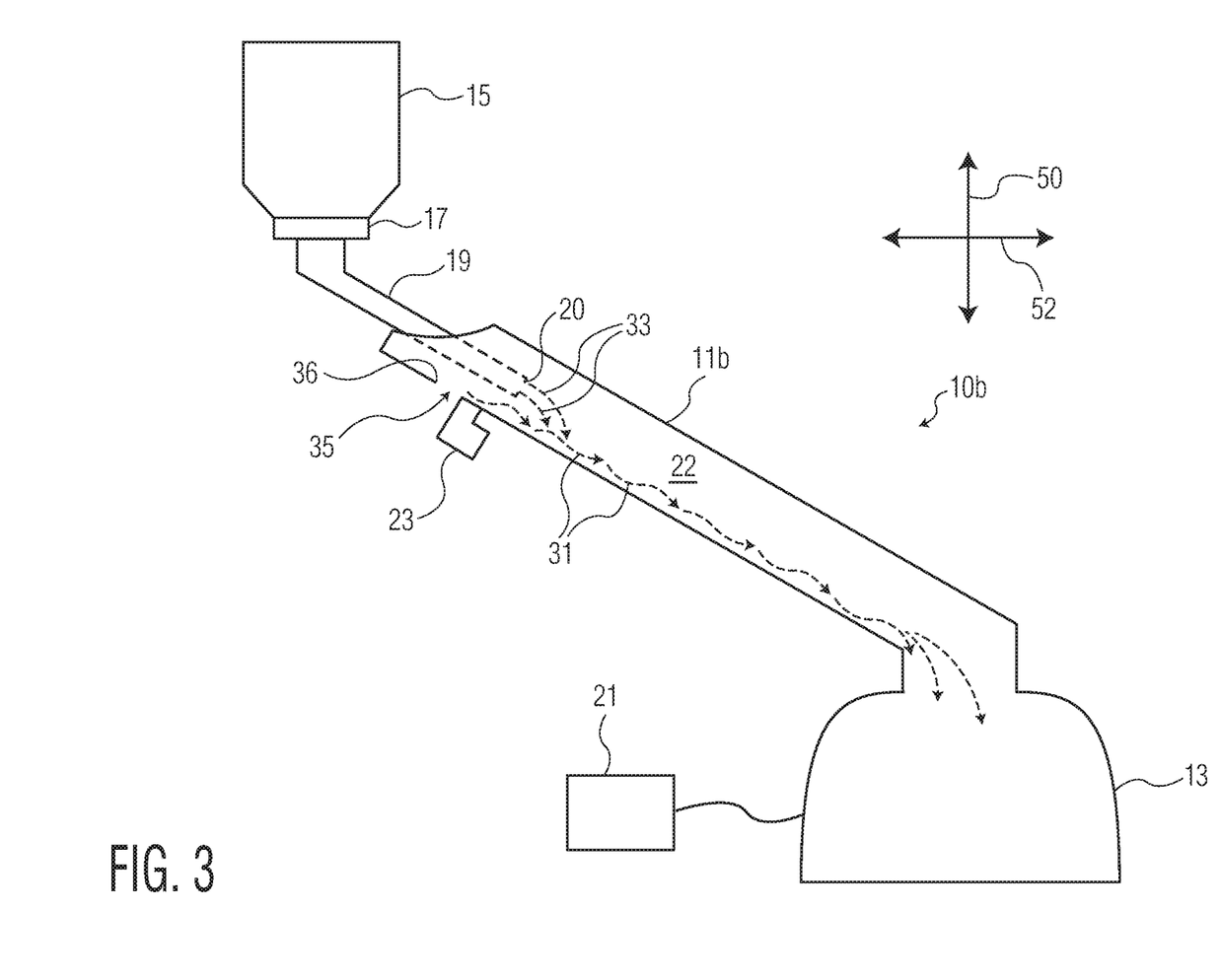
FIG. 3 is a diagram of another exemplary particulate material conveying system according to the present disclosure.

FIGS. 1 and 3 depict exemplary particulate material conveying apparatuses 10a and 10b, respectively. Each of the particulate material conveying apparatuses 10a and 10b comprise a slide duct 11a, 11b and an air movement mechanism 23. As can be seen, the slide duct 11a, 11b extends between a proximal end 24 and a distal end 26 in both a horizontal direction 52 and a vertical direction 50 in order to convey particulate material at least by gravity through the particulate material conveying apparatuses 10a, 10b. In some embodiments, the particulate material conveying apparatuses 10a, 10b may further comprise a particulate material hopper system and may terminate at a destination in order to provide transport of particulate material to the destination. For example, the particulate material conveying apparatuses 10a, 10b may further comprise hopper 15, which is a source of particulate material, terminate at a forming chamber 13 where the particulate material is used as part of a process to form an absorbent core or an absorbent core pre-cursor product.

The hopper 15 in FIGS. 1 and 3 may generally be suited to contain particulate material, such as SAM particles or other particulate material. The hopper 15 may be connected to a particulate material delivery conduit 19. The particulate material delivery conduit 19 may transport the particulate material from the hopper 15 to the slide duct 11a, 11b of the particulate material conveying apparatuses 10a, 10b. In at least some embodiments, the conduit 19 may be angled such that the particulate material traverses through the conduit 19 by gravity and exits the conduit distal end 20, also termed an outlet herein, into the slide duct 11a, 11b. In at least some of these embodiments, the conduit distal end 20 may be disposed vertically above the slide duct bottom wall 12 such that the particulate material exiting the conduit distal end 20, represented by arrows 33, falls onto the slide duct bottom wall 12.

A particulate metering device 17 may be disposed between the hopper 15 and the conduit 19 in some embodiments. Where present, the metering device 17 may ensure that only a specified amount (for instance, by volume or by weight) of particulate material flows through the conduit 19 per unit of time, in order to ensure a desired amount of particulate material reaches the forming chamber 13 over each given time unit. Some example suitable ranges for the volume of particulate material flowing through the metering device 17 are between about 5,000 grams per minute (g/min) and about 25,000 g/min.

The forming chamber 13 is where absorbent cores or absorbent core pre-cursor components may be made using the particulate material transported from the hopper 15 by the particulate material conveying apparatuses 10a or 10b. Such forming chambers are generally known in the absorbent core forming art and can be configured in many different ways. In some such embodiments, the forming chamber 13 may include equipment such as a vacuum forming table or vacuum forming drum. Accordingly, in some embodiments, the forming chamber 13 may be connected to a vacuum source, such as vacuum source 21, to provide a vacuum to the forming chamber (i.e. produce a negative pressure—relative to atmospheric pressure—within the forming chamber), and more specifically to the forming table/drum. The negative pressure within the table/drum provides suction to pull and/or direct the particulate material entering the forming chamber 13 from the particulate material conveying apparatuses 10a or 10b to locations on the forming table/drum. In this manner, particulate material may be drawn onto the table/drum to form absorbent cores or absorbent core pre-cursor components. Additionally, due to the fluid-interconnected nature of the forming chamber 13 and the slide duct 11a, 11b, the interior region of the slide duct 11a, 11b may also have a negative pressure. In such embodiments, it is evident that as the particulate material enters the particulate material conveying apparatuses 10a, 10b from the conduit 19, the particulate material then enters the slide duct 11a, 11b while the interior region of the slide duct 11a, 11b is under negative pressure.

Figure 2:
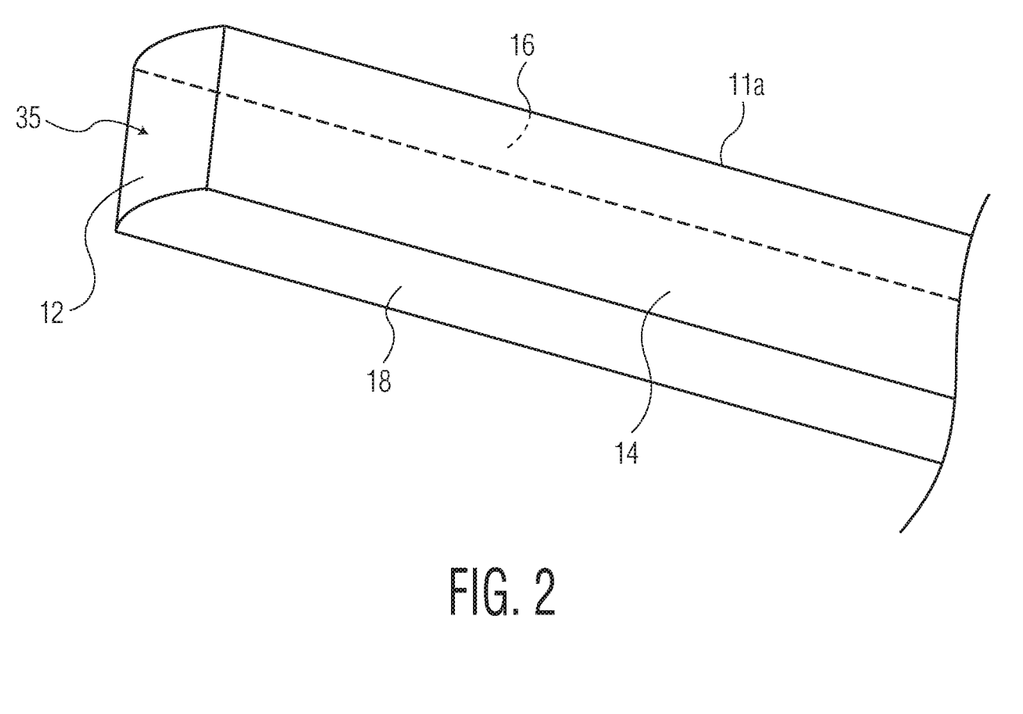
FIG. 2 is a perspective view of the slide duct of the particulate material conveying system of FIG. 1.
Figure 4:
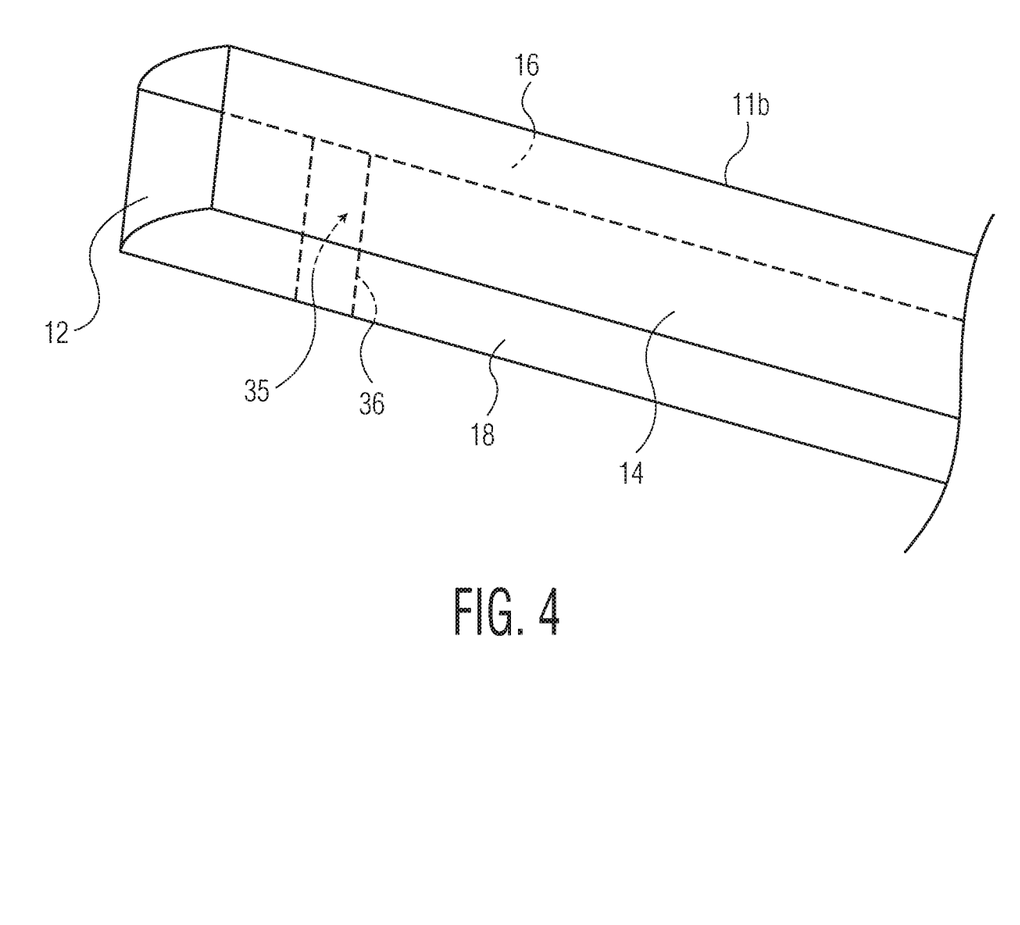
FIG. 4 is a perspective view of the slide duct of the particulate material conveying system of FIG. 3.

FIGS. 2 and 4 are perspective views of alternative embodiments of a slide duct according to the present disclosure, slide ducts 11a and 11b, respectively. In general, the slide ducts 11a, 11b may comprise a slide duct bottom wall 12, a slide duct top wall 14, a slide duct first side wall 16, and a slide duct second side wall 18. However, in other embodiments, the slide ducts 11a, 11b may not be fully enclosed. For instance, the slide ducts 11a, 11b may only comprise a slide duct bottom wall 12 and slide duct first and second walls 16, 18. The walls 12, 16, 18 (and 14 in some embodiments) may bound interior region 22 of the slide duct 11.

In the embodiments shown in FIGS. 2 and 4, the slide ducts 11a, 11b are shown as generally having a rectangular shape. However, it should be understood that the described shape is not meant to be limiting. In general slide ducts 11a, 11b may have any suitable shape, such as circular, triangular, trapezoidal, or the like. However, it will be evident from the present disclosure that embodiments where the slide duct bottom wall 12 is generally flat may be preferred embodiments.

The slide ducts 11a, 11b may be comprised of any suitable material, such as metal or plastic. For example, where the slide ducts 11a, 11b are comprised of metal, the slide ducts 11a, 11b may be aluminum or steel or the like. Where the slide ducts 11a, 11b are plastic, the slide ducts 11a, 11b may be high-density polyethylene (HDPE) or polyvinyl chloride (PVC) or the like. In general, the slide ducts 11a, 11b may be comprised of any suitable low-friction material allowing the particulate material to slide down the slide ducts 11a, 11b when the slide ducts are oriented at any of the angles described herein with respect to the horizontal direction 52.

The slide ducts 11a, 11b may further comprise an opening 35. The opening 35 may be the opening through which air enters the slide ducts 11a, 11b due to the air movement mechanism 23. In the embodiment of FIG. 2, the opening 35 is the proximal end 24 of the slide duct 11a. As can be seen in FIG. 1, the air movement mechanism 23 of particulate material conveying apparatus 10a is disposed proximate the proximal end 24 of the slide duct 11a and is configured to inject air into the interior region 22 through the proximal end 24 (e.g. opening 35). In the embodiment of FIG. 4, the opening 35 comprises an aperture 36 in the slide duct bottom wall 12 of the slide duct 11b. As can be seen in FIG. 3, the air movement mechanism 23 of particulate material conveying apparatus 10b is disposed proximate the opening 35 and is configured to inject air into the interior region 22 through the opening 35.

In general, the air movement mechanism 23 may be configured to inject air into the interior region 22 of the slide ducts 11a, 11b. In some embodiments, the air movement mechanism 23 may comprise an air knife configured to direct air into the interior region 22 of the slide duct 11a, 11b. In other embodiments, the air movement mechanism 23 may comprise an air blower, such as a fan or other air movement source, and may comprise one or more nozzles that are disposed proximate the opening 35 to direct air into the interior region 22 of the slide duct 11a, 11b.

Figure 5:
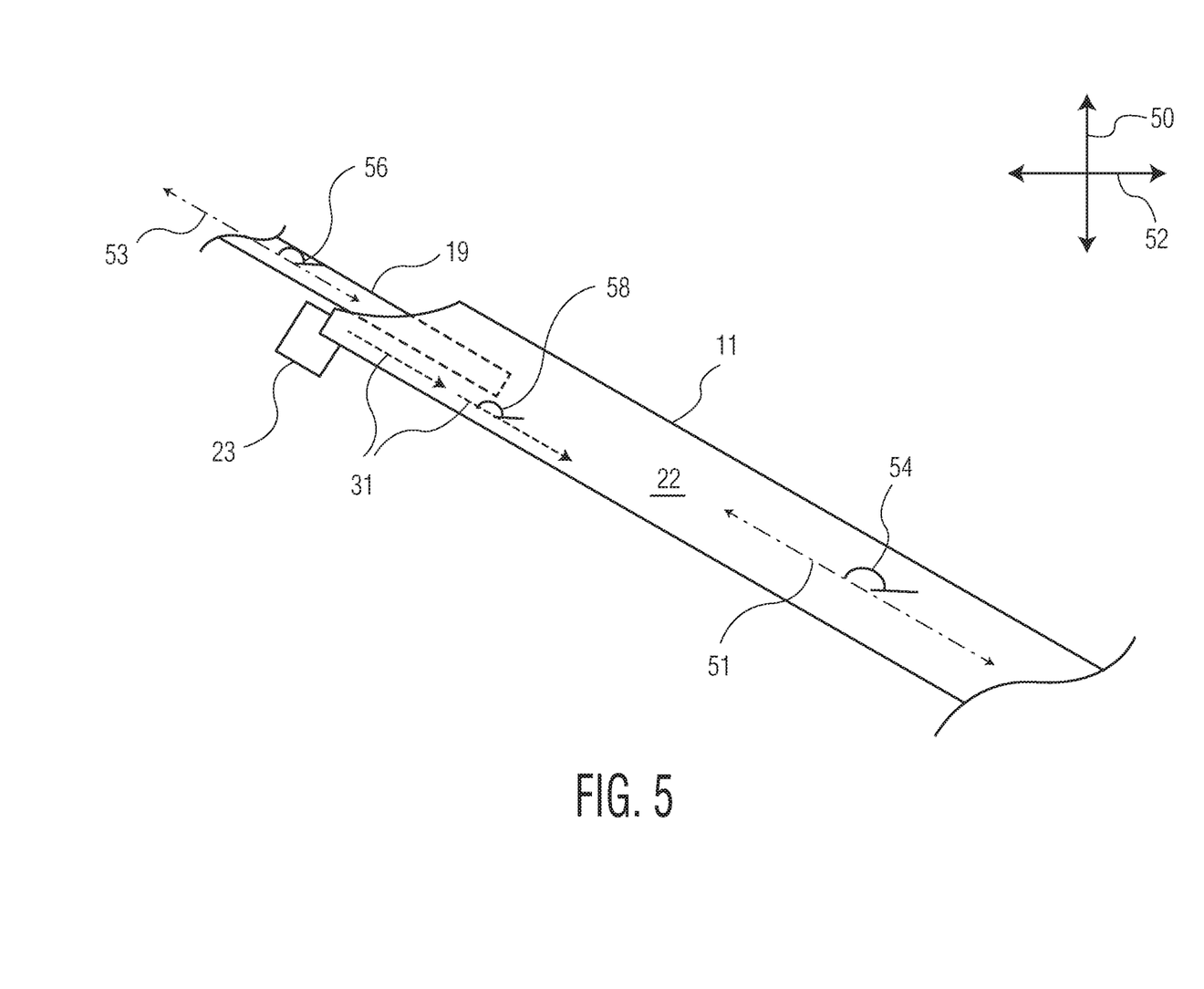
FIG. 5 is a side-view of a portion of the particulate material conveying system of FIG. 1.

As can be seen in more detail in FIG. 5, the slide duct 11a, 11b and the conduit 19 may each have an axis, slide duct axis 51 an conduit axis 53, respectively. FIG. 5 additionally depicts air movement mechanism 23 and the direction of the air, represented by arrows 31, injected into the interior region 22 of the slide duct 11a, 11b. As can be seen, the air movement mechanism 23 is configured to inject the air into the interior region 22 of the slide duct 11a, 11b in the general direction of the slide duct axis 51, and the air movement mechanism 23 is disposed closer to the proximal end 24 of the slide duct 11a, 11b than the conduit distal end 20. In such embodiments, as the particulate material exits the conduit distal end 20, the particulate material falls onto the moving air stream in the interior region 22 formed by the air movement mechanism 23. In this configuration, as the particulate material falls onto the moving airstream, the particulate material is swept in the general direction of the moving air. By configuring the particulate material conveying apparatuses 10a, 10b such that the particulate material falls onto a moving air stream, the particulate material experiences less rebounding effect from striking the slide duct bottom wall 12 from its fall from the conduit 19. This reduced rebounding by the particulate material allows for more precise control of the particulate material as it moves along the slide duct 11 and into the forming chamber 13, and ultimately in its placement within an absorbent core or absorbent core pre-cursor product.

Figure 6:
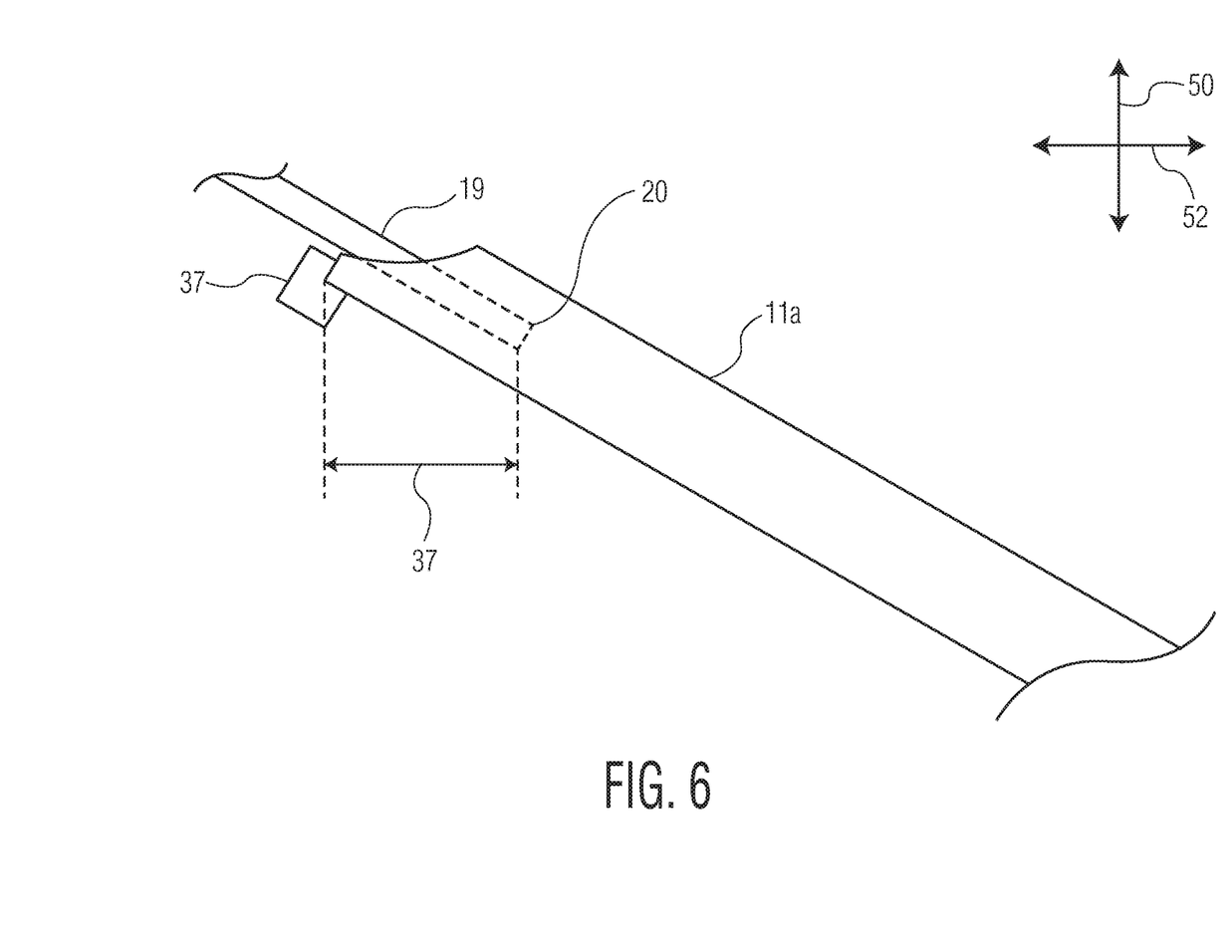
FIG. 6 is another side-view of a portion of the particulate material conveying system of FIG. 1.

FIG. 6 further details possible locations of the air movement mechanism 23 in relation to the conduit 19. More specifically, the opening through which the air movement mechanism 23 injects air into the interior region 22 of the slide duct 11a, 11b may be disposed a horizontal distance 37 from the conduit distal end 20. In some embodiments, the horizontal distance 37 may be between about 15 mm to about 3 meters, or between about 15 mm and about 2 meters, or between about 15 mm and about 1 meter, or between about 20 mm and about 500 mm. In general, the horizontal distance 37 may be any suitable distance such that the particulate material exiting the conduit distal end 20 falls onto the stream of air injected into the interior region 22 of the slide duct 11a, 11b by the air movement mechanism 23.

Turning back to FIG. 5, it can be seen that the slide duct axis 51 may be oriented at an angle 54 with respect to the horizontal direction 52. The angle 54 may be between about 100 degrees and about 175 degrees, or between about 110 degrees and about 170 degrees, or between about 120 degrees and about 165 degrees, or between about 125 degrees and about 160 degrees. Further, in different embodiments, the conduit axis 53 may form an angle 56 with respect to the horizontal direction 52 and could be any of the angles described with respect to angle 54. The angle 56 may be the same as angle 54 in some embodiments, while in other embodiments, the angle 56 may differ from the angle 54.

FIG. 5 further depicts the direction of the air injected into the interior region 22 of the slide duct 11 by the air movement mechanism 23, as represented by arrows 31. The direction of the injected air may form an angle 58 with respect to the horizontal direction 52. The angle 58 may also be any of the angles described with respect to angle 54. Additionally, in some embodiments, the angle 58 may be the same as the angle 54, while in other embodiments the angle 58 may differ from the angle 54. In such embodiments where the angle 58 differs from the angle 54, the angle 58 may differ by between about plus or minus one (1) degree to about plus or minus thirty (30) degrees from the angle 54, or between about plus or minus one (1) degree to about plus or minus ten (10) degrees from the angle 54.

Another advantage of the present particulate material conveying apparatuses 10a and 10b is that the air movement mechanism 23 may only need to operate at relatively low energy to achieve desirable results. For instance, the air movement mechanism 23 may be configured to supply the air into the interior region 22 of the slide duct 11a, 11b at a pressure of between about 0.5 pounds per square inch (psi) (3.45 kPa) and about 25 psi (172 kPa), or between about 1 psi (6.89 kPa) and about 25 psi (172 kPa), or between about 1 psi (6.89 kPa) and about 20 psi (138 kPa), or between about 1 psi (6.89 kPa) and about 15 psi (103 kPa), or between about 1 psi (6.89 kPa) and about 10 psi (68.9 kPa).

Figure 7:
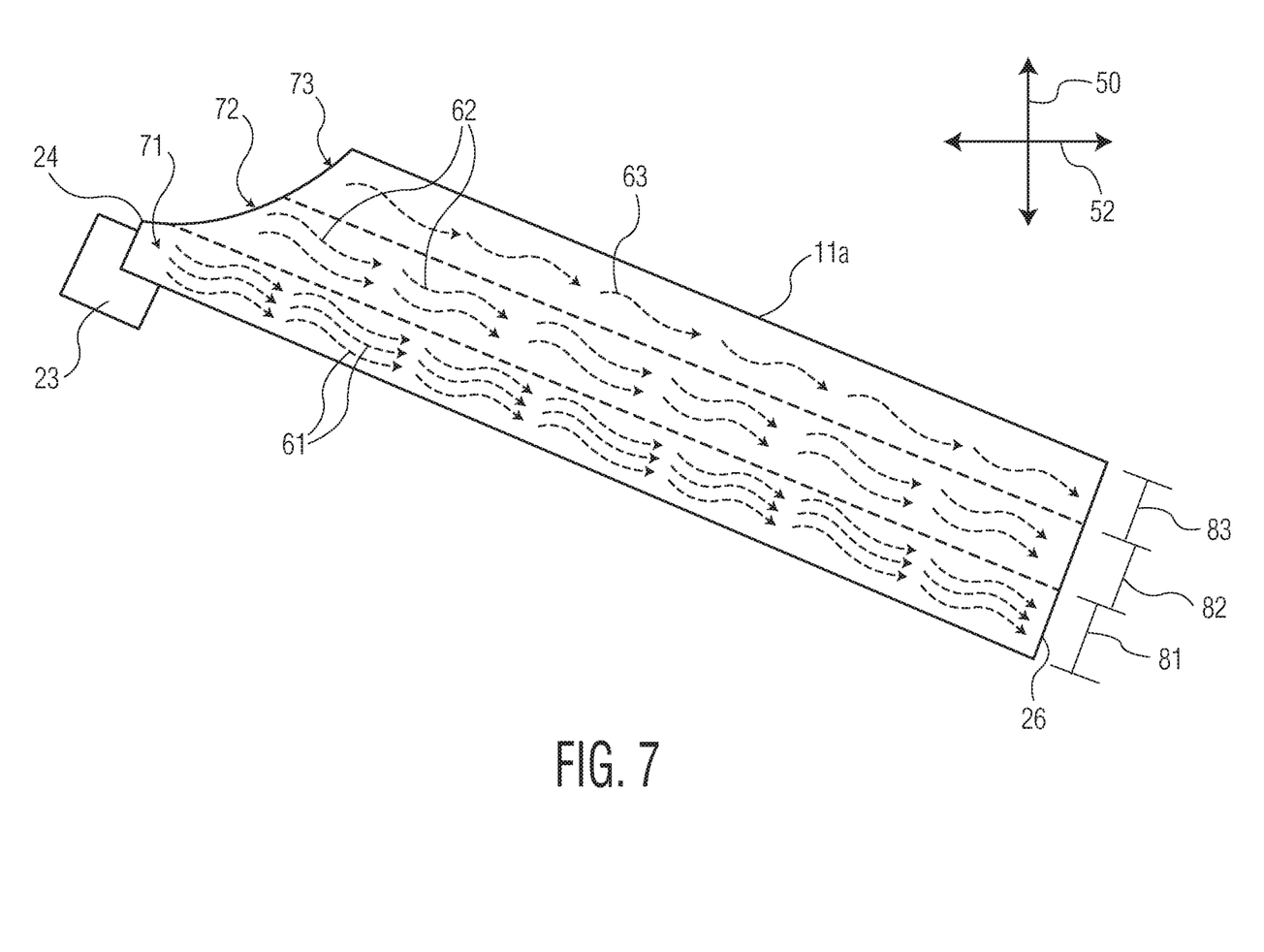
FIG. 7 is another side-view of the slide duct of the particulate material conveying system depicting relative airflow volumes in different regions of the slide duct.

FIG. 7 is a diagram of relative airflows within the slide duct 11a due to the air movement mechanism 23. It should be understood that although the example of FIG. 7 is directed toward slide duct 11a, the description applies equally to slide duct 11b. The slide duct 11a may be broken in three separate regions stacked on top of each other. For instance, the slide duct 11a may have a slide duct bottom region 71, a slide duct middle region 72, and a slide duct top region 73. Each of the regions 71, 72, and 73 extend from the proximal end of the duct 24 to the distal end of the duct 26 and extend parallel to the slide duct axis 51. Each of the regions 71, 72, and 73 has a corresponding height 81, 82, and 83, which are measured perpendicularly to the slide duct axis 51. In the example of FIG. 7, each of the regions 71, 72, and 73 have heights 81, 82, and 83 which are one-third of an overall height of the slide duct 11a.

Arrows 61, 62, and 63 depict relative amounts of airflow within the slide duct 11a during operation, e.g. while the air movement mechanism 23 is injecting air into the interior region 22 of the slide duct 11a. As can be seen, relatively more air is flowing through, and exiting, the slide duct bottom region than in either of the other region 82 or 83. This is because, as described previously, the air injected into the interior region 22 of the slide duct 11a is directed generally in the direction of the slide duct axis 51. Additionally, as can be seen throughout the FIGS., the air movement mechanism 23 is disposed such that the air injected into the interior region 22 is mostly injected into the slide duct bottom region 71. In such embodiments, the injected air tends to stay within the slide duct bottom region 71. In some further embodiments, not only is relatively more air is flowing through, and exiting, the slide duct bottom region than in either of the other region 82 or 83, but a majority of the air flowing through the slide duct 11a may flow through, and exit, the slide duct bottom region 71—that is more air flows through and exits the slide duct bottom region 71 the air flowing through and exiting the slide duct middle and top regions 82 and 83 combined.

One way of measuring the amount of air flowing through and exiting each of the regions 71, 72, and 73 is to position pitot tubes at the distal end 26 of the slide duct 11a. For example, a pitot tube may be positioned at the distal end 26 of the slide duct 11a in the center of each of the regions 71, 72, 73. Measurements from the pitot tube can be used to calculate a flow rate as is well known in the art. The flow rates through the different regions 71, 72, and 73 can then be used to determine an amount of air flowing through and exiting each of the regions 71, 72, and 73 (for instance, per unit of time), which can be compared to determine whether the amount of air flowing through the region 71 is greater than the amount of air flowing through either of the other regions 82, 83 and/or both of the regions 82, 83 combined.

Figure 8:
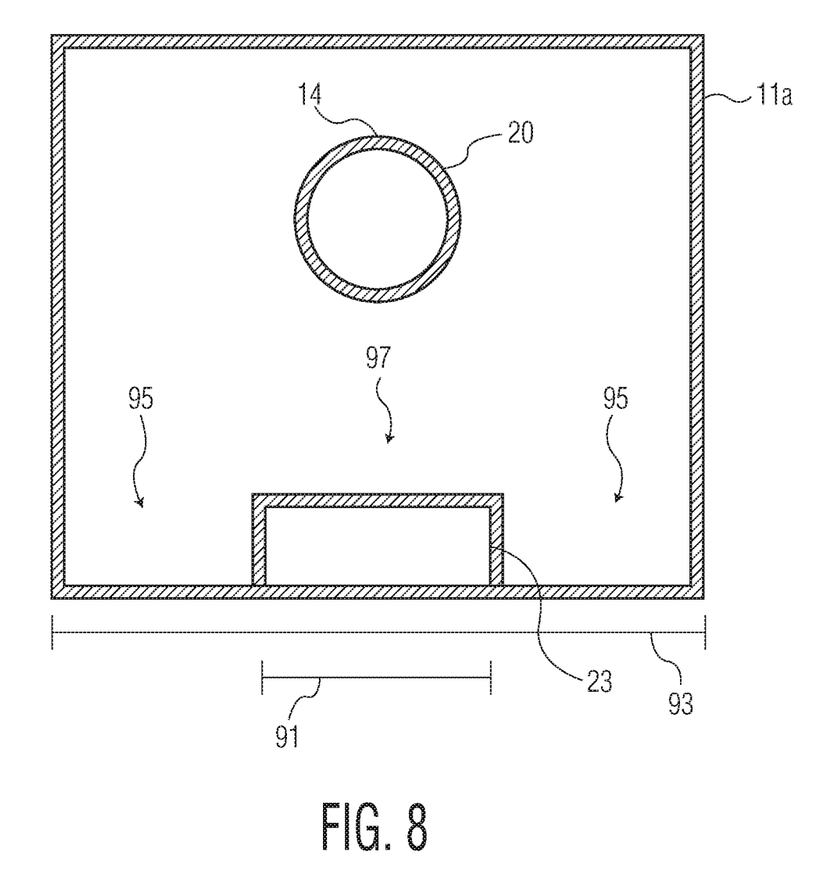
FIG. 8 is straight-on view of the inside of the slide duct of FIG. 1 looking toward the slide duct proximal end.

FIG. 8 is straight-on view of the inside of slide duct 11a, looking toward the slide duct proximal end 26 with a view of a portion of the air movement mechanism 23. As can be seen in FIG. 8, the air movement mechanism 23 may have a mechanism width 91, while the slide duct 11a may have a slide duct with 93. The portion of the slide duct 11a that the air movement mechanism 23 spans is termed the central slide duct region 97, while the portions of the slide duct 11a where the air movement mechanism 23 does not span are termed side regions 95.

In some embodiments, the mechanism width 91 may be the same as the slide duct with 93 such that air injected into the slide duct 11a spans the entire slide duct with 93. However, in other embodiments, the mechanism width 91 may be less than the slide duct with 93, as is shown in FIG. 8. For instance, the mechanism width 91 may be between about 50% and about 90% of the slide duct with 93, or between about 50% and about 80% of the slide duct with 93, or between about 50% and about 75% of the slide duct with 93. In such embodiments where the mechanism width 91 is less than the slide duct with 93, the air injected into the interior region 22 of the slide duct 11a will not span the entire slide duct with 93. For instance, most of the injected air will only span through the central region 97. Although, it should be understood that the side regions 95, where there is an absence of injected air, will have some airflow—due to entrainment of air in those side regions 95 by the injected air, spreading of the injected air in a width-wise manner across the slide duct 11a, and due to negative pressure within the interior region 22 (if present). However, the airflow through the side regions 95 will be less than the airflow through the central region 97. Accordingly, this may allow for further control of the particulate material—for example, a greater amount of particulate material may deposit in a more central region of an absorbent core or absorbent core pre-cursor product as relatively more particulate material may be transported through the central region 97 than the side regions 95 due to the greater air flow within the central region 97.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. A particulate material conveying apparatus comprising:
a slide duct extending between a proximal end and a distal end and having a slide duct axis extending in both a vertical direction and a horizontal direction, the slide duct comprising:
an interior region bounded at least in part by a slide duct wall, the interior region having a top third interior region extending along the slide duct axis, a middle third interior region extending along the slide duct axis, and a bottom third interior region extending along the slide duct axis, each interior region extending between the proximal end and the distal end of the slide duct, wherein the top third interior region is disposed above the middle third interior region in the vertical direction and wherein the middle third interior region is disposed above the bottom third interior region in the vertical direction,
an opening defined by the slide duct wall, and
a particulate material outlet through which particulate material enters the interior region of the slide duct, wherein the particulate material outlet is disposed closer to the distal end of the slide duct than the opening; and
an air movement mechanism configured to move air through the opening and into the interior region of the slide duct in a direction of the slide duct axis such that of the air exiting the slide duct distal end a greater amount of air exits through the bottom third interior region than either of the top third interior region or the middle third interior region.

2. The particulate material conveying apparatus of claim 1, wherein a majority of the air exiting the slide duct distal end exits through the bottom third interior region.

3. The particulate material conveying apparatus of claim 1, wherein the proximal end of the slide duct defines the opening.

4. The particulate material conveying apparatus of claim 1, wherein the opening comprises an aperture in the slide duct wall.

5. The particulate material conveying apparatus of claim 1, wherein the air movement mechanism is an air-knife.

6. The material conveying apparatus of claim 1, wherein the air movement mechanism is configured to supply air to the opening at a pressure of between about 1 pounds per square inch (psi) and about 25 psi.

7. The material conveying apparatus of claim 1, wherein the air movement mechanism is configured to supply air to the opening at a pressure of between about 1 pounds per square inch (psi) and about 15 psi.

8. The material conveying apparatus of claim 1, wherein the air movement mechanism is configured to supply air to the opening at a pressure of between about 1 pounds per square inch (psi) and about 5 psi.

9. A particulate material conveying apparatus comprising:
a slide duct extending between a proximal end and a distal end and having a slide duct axis extending in both a vertical direction and a horizontal direction, the slide duct comprising an interior region bounded at least in part by a slide duct wall, the slide duct wall defining an opening, and a material outlet through which material enters the interior region of the slide duct and wherein the material outlet is disposed closer to the distal end of the slide duct than the opening;
an air movement mechanism configured to move air through the opening and into the interior region of the slide duct, wherein the air enters th interior region of the slide duct at an angle of between about 0 degrees and about 30 degrees with respect to the slide duct axis,
wherein the air movement mechanism is configured to supply air to the opening at a pressure of between about 1 pounds per square inch (psi) and about 20 psi.

10. The particulate material conveying apparatus of claim 9, wherein the air movement mechanism comprises a nozzle, and wherein the nozzle is disposed proximate the opening and orientated at an angle of between about 0 degrees and about 10 degrees with respect to the slide duct axis.

11. The particulate material conveying apparatus of claim 9, wherein the air movement mechanism is an air-knife.

12. The particulate material conveying apparatus of claim 9, wherein the air movement mechanism is an air blower.

13. The particulate material conveying apparatus of claim 9, wherein at least a portion of the interior region of the slide duct is under negative pressure.

14. The material conveying apparatus of claim 9, wherein the air movement mechanism is configured to supply air to the opening at a pressure of between about 1 psi to about 25 psi.

15. The material conveying apparatus of claim 9, wherein the air movement mechanism is configured to supply air to the opening at a pressure of between about 1 psi to about 15 psi.

16. A particulate material conveying system comprising:
a hopper connected to a conduit, the conduit extending between a proximal end connected to the hopper and a distal end;
a slide duct extending between a proximal end and a distal end and having a slide duct axis, the slide duct comprising an interior region bounded at least in part by a slide duct wall, the slide duct wall defining an opening;
an air movement mechanism configured to move air through the opening and into the interior region of the slide duct; and
a vacuum source connected to the slide duct distal end, wherein the air movement mechanism is configured to move the air into the interior region of the slide duct at an angle of between about 0 degrees and about 30 degrees with respect to the slide duct axis,
wherein the air movement mechanism is configured to supply the air to the opening at a pressure of between about 1 pounds per square inch (psi) and about 25 psi, wherein the outlet is disposed between the slide duct proximal end and the slide duct distal end.

17. The particulate material conveying system of claim 16, wherein the outlet distal end is disposed closer to the slide duct distal end than the opening.

18. The particulate material conveying system of claim 16, wherein the air movement mechanism is an air knife.

* * * * *